US00PP33207P2

(12) United States Plant Patent
Mathey

(10) Patent No.: US PP33,207 P2
(45) Date of Patent: Jun. 29, 2021

(54) ***HYDRANGEA* 'SMNHPH'**

(50) Latin Name: *Hydrangea paniculata*
Varietal Denomination: SMNHPH

(71) Applicant: Spring Meadow Nursery Inc., Grand Haven, MI (US)

(72) Inventor: Megan Mathey, Holland, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/039,343

(22) Filed: Sep. 30, 2020

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Cassandra Bright

(57) ABSTRACT

A new and distinct cultivar of *Hydrangea* plant named 'SMNHPH' is disclosed, characterized by thick foliage, a compact plant habit and thick stems. Inflorescences mature to an attractive deep, rich pink. The new variety is a *Hydrangea*, normally produced as an ornamental plant.

4 Drawing Sheets

Latin name of the genus and species: *Hydrangea paniculata.*

Variety denomination: 'SMNHPH'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new habits and interesting colors. The crossing resulting in this new variety was made during July of 2013.

The seed parent is *Hydrangea paniculata* 'SMNHPPINO' U.S. Pat No. 27,302. The pollen parent is *Hydrangea paniculata* 'Red Swan', unpatented. The new variety was identified as a potentially interesting selection in the Summer of 2016, at a commercial greenhouse in Grand Haven, Mich.

Asexual reproduction of the new cultivar 'SMNHPH' by vegetative softwood cuttings was first performed during the Summer of 2016, at a commercial greenhouse in Grand Haven, Mich. Subsequent asexual propagation has shown that the unique features of this cultivar are stable and reproduced true to type in four successive generations. Date of first sale was Jun. 23, 2020, occurring in the United States. This sale was made directly by the inventor or one who obtained the claimed invention directly or indirectly from the inventor. This sale and all public disclosures made between Jun. 23, 2020 and the filing of this application fall within the exception allowed under 102(b)(1).

SUMMARY OF THE INVENTION

The cultivar 'SMNHPH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPH' These characteristics in combination distinguish 'SMNHPH' as a new and distinct *Hydrangea* cultivar:

1. Compact plant habit.
2. Flowers age attractively to a rich, deep pink.
3. Thick, durable foliage.
4. Strong stems.

PARENT COMPARISON

Plants of the new cultivar 'SMNHPH' are similar to plants of the seed parent in most horticultural characteristics, however, plants of the new cultivar 'SMNHPH' differ in the following;

1. The new variety has flowers which turn a richer red-pink in the Fall, compared to the pale pink flower color of the seed parent in the Fall.
2. The new variety has thicker, lighter green foliage than the seed parent.

Plants of the new cultivar 'SMNHPH' are similar to plants of the pollen parent in most horticultural characteristics, however, plants of the new cultivar 'SMNHPH' differ in the following;

1. The new variety has flowers which stay white longer before turning a rich red-pink; flowers of the pollen parent turn pink earlier.
2. The new variety has larger flowers than the pollen parent.

COMMERCIAL COMPARISON

Plants of the new cultivar 'SMNHPH' can be compared to the variety *Hydrangea paniculata* 'Jane', U.S. Pat. No. 22,330. These varieties are similar in most horticultural characteristics; however, 'SMNHPH' differs in the following:

1. The new variety has larger inflorescences than this comparator.
2. Flowers of the new variety hold their color longer than this comparator.

3. Stems of the new variety are stronger than stems of 'Jane'.

BRIEF DESCRIPTION OF THE PHOTOGRAPHS

'SMNHPH' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years. All plants were container grown in Grand Haven, Mich. and photographed during 2020.

DETAILED BOTANICAL DESCRIPTION

Figure 1:
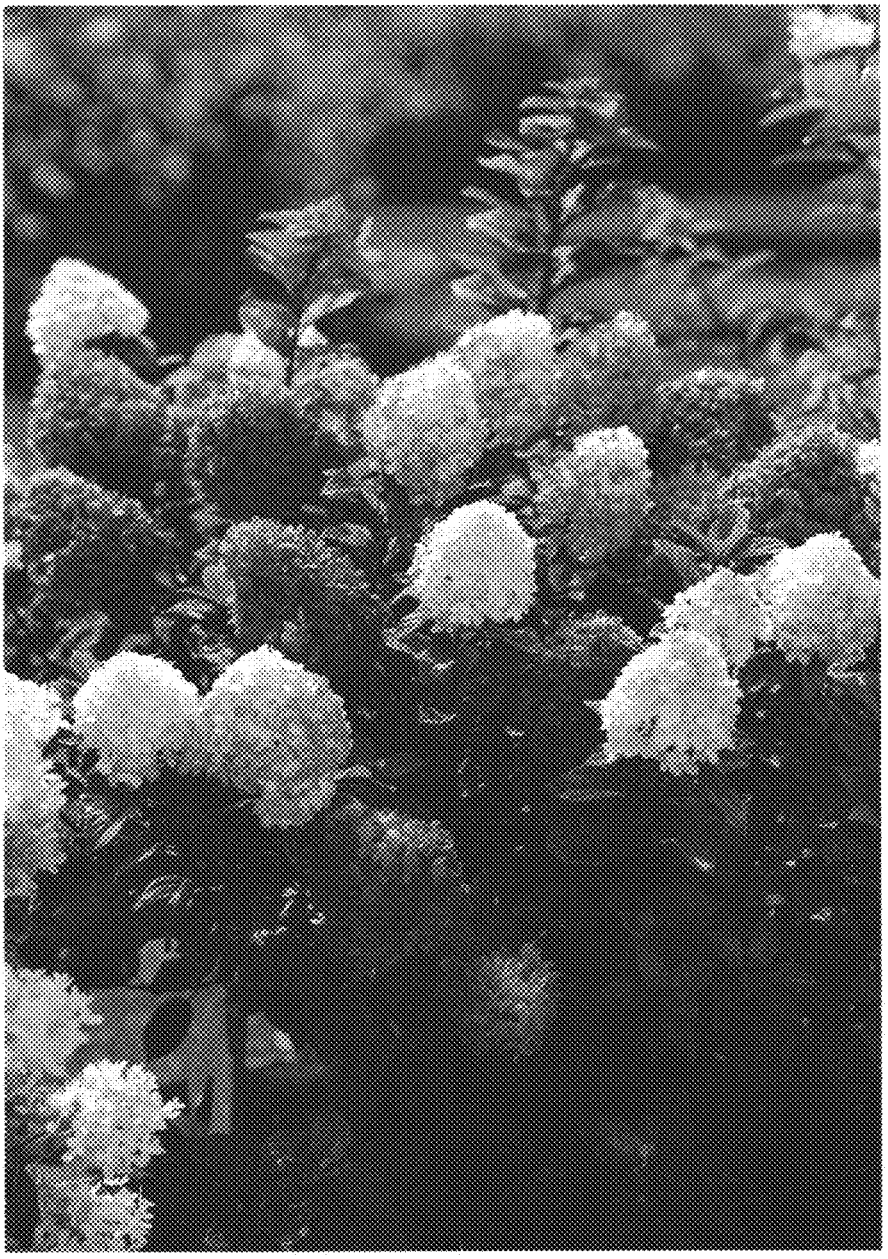
FIG. 1 shows plants of 'SMNHMP' grown outdoors in Grand Haven, Mich. during early Fall(second week of September). Plants have both white and pink flowers.
Figure 2:
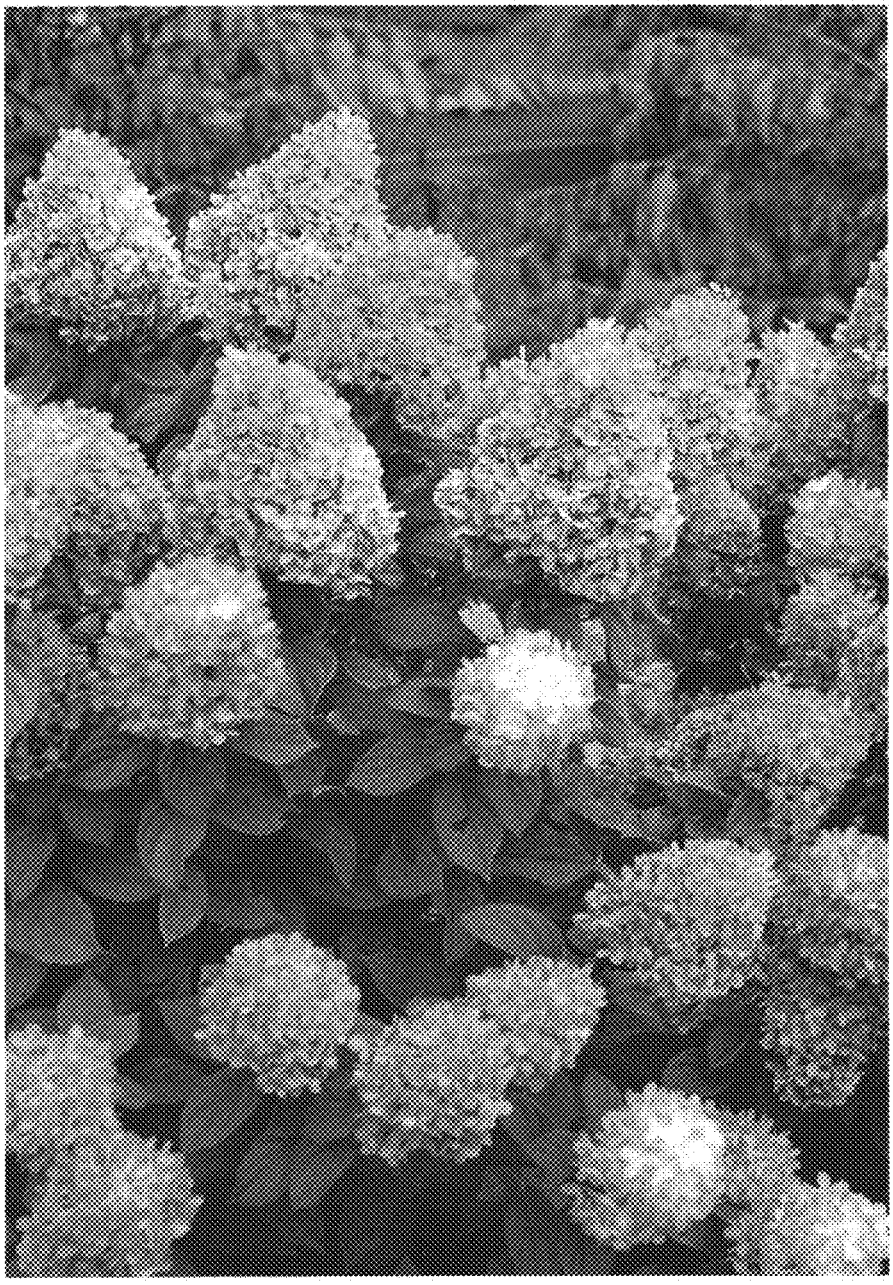
FIG. 2 shows the inflorescence color of the plants in FIG. 1 approximately 10 days earlier, before the rich pink color forms.
Figure 3:
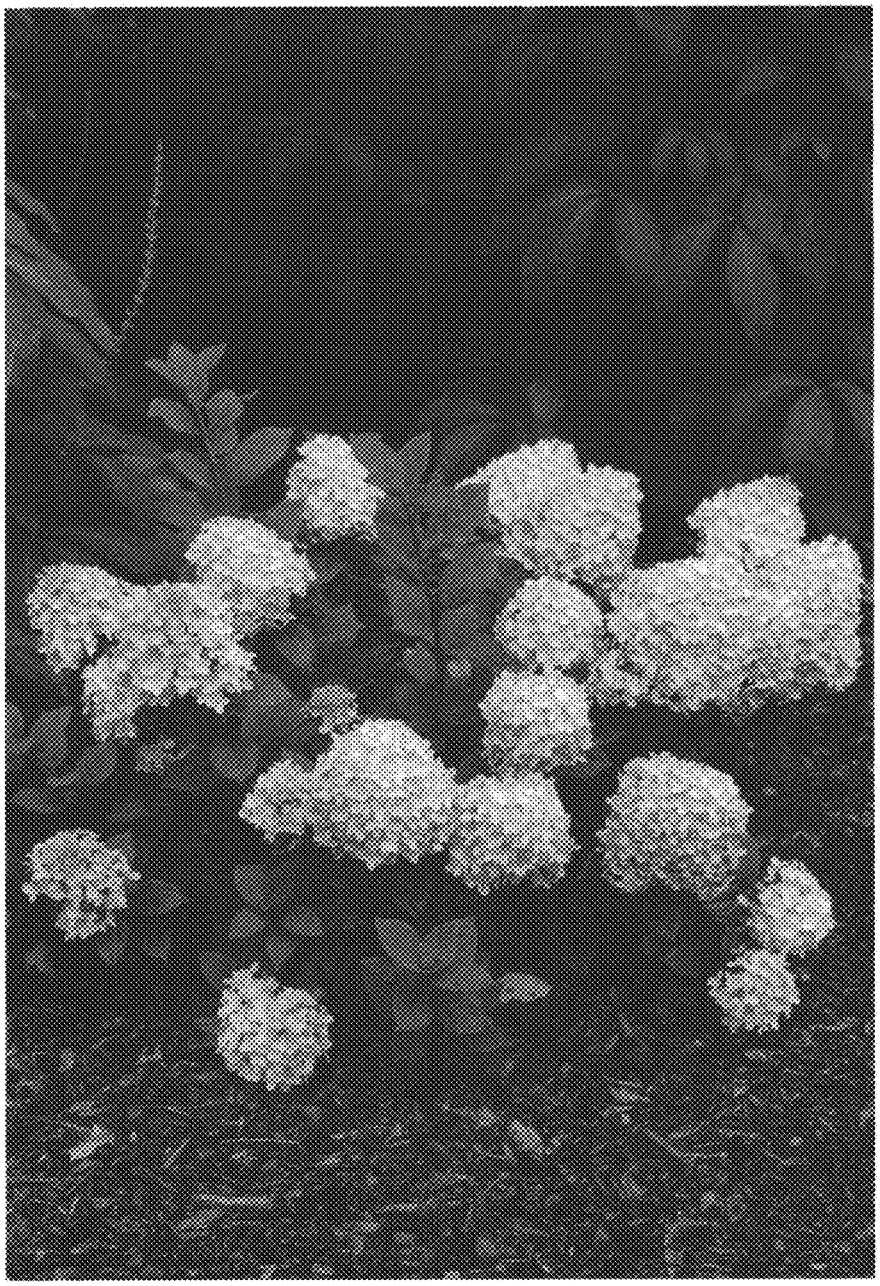
FIG. 3 shows the early Summer(mid-July) color of a mature inflorescence color of a container-grown plant.
Figure 4:
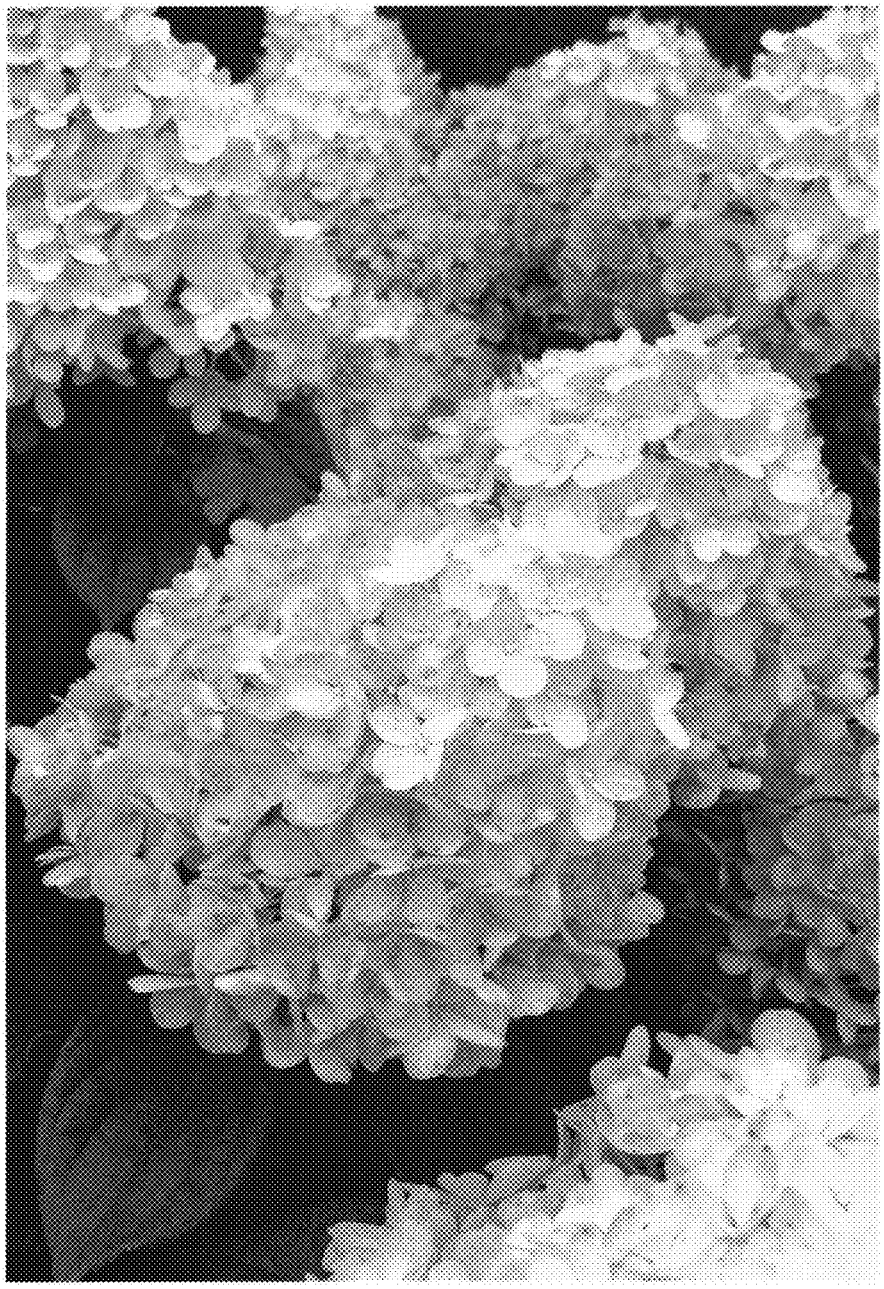
FIG. 4 shows the late Summer(late August) color of a maturing inflorescence, just beginning to change color of a container-grown plant.

In the following description, color references are made to The Royal Horticultural Society Color Chart 2015 except where general terms of ordinary dictionary significance are used. The following observations and measurements describe 'SMNHPH' plants grown in a commercial poly greenhouse in Grand Haven, Mich. under natural lighting. Measurements were taken during Summer of 2020. The plants were about 2.5 years old, growing in 3-gallon pots. The growing temperature ranged from 5° C. to 27° C. Measurements and numerical values represent averages of typical plant types.

Botanical classification: *Hydrangea paniculata* 'SMNHPH'.

PROPAGATION

Time to initiate roots: Approximately 18 days at about 18° to 27° C.

Time to produce a rooted young plant: Approximately 60 days at about 18° to 27° C.

Propagation method: Softwood cuttings.

PLANT

Plant type: Flowering deciduous perennial shrub.
Growth habit: Upward and outward.
Overall plant shape: Upright, rounded, compact.
Height: 68 cm.
Plant spread: 97 cm.
Growth rate: Good.
Plant vigor: Moderate to vigorous.
Branching habit: Upright, outward.
Length of primary lateral branches: 55 cm.
Diameter of lateral branches: 5 mm.
Quantity of lateral branches: 30 to 40.
Stem:
- *Stem shape.*—Round.
- *Stem strength.*—Strong.
- *Color.*—Immature: RHS Grey-Brown N199C. Mature: RHS Grey-Brown 199B.
- *Pubescence.*—None.
- *Angle of attachment.*—15° to 45°.

Internode length: Average 3 cm.

Root description: Moderately dense, thick main roots with fine, fibrous secondary roots. Main roots colored near Brown 200D, secondary roots near Yellow-White 158D.

FOLIAGE

Leaf:
- *Arrangement.*—Opposite.
- *Leaf shape.*—Elliptic.
- *Average length.*—4.5 cm.
- *Average width.*—3.75 cm.
- *Apex.*—Cuspidate.
- *Base.*—Obtuse.
- *Margin.*—Serrate.
- *Texture of top surface.*—Rough pubescent.
- *Texture of bottom surface.*—Leathery with distinct veins.
- *Color.*—Young foliage upper side: RHS Green 137B. Young foliage under side: RHS Yellow-Green 147B. Mature foliage upper side: RHS Green 137B. Mature foliage under side: RHS Yellow-Green 147D.
- *Venation.*—Pattern: Pinnate. Color upper side: RHS Yellow-Green 151C. Color under side: RHS Yellow-Green 145C.
- *Petiole.*—Average Length: 7 mm. Diameter: 2 mm. Petiole color upper side: RHS Green 143C slightly flushed Green-Purple 183C. Petiole color lower side: RHS Green 143C. Petiole Texture upper side: Smooth. Petiole Texture lower side: Slightly pubescent.

FLOWER

Natural flowering season: Summer until Fall.

Inflorescence:

Panicle:
- *Shape.*—Very broad deltate.
- *Height.*—13 cm.
- *Diameter.*—11 cm.
- *Quantity of flowers per inflorescence.*—Fertile flowers: About 100. Sterile flowers: 200 to 500.
- *Persistent or self-cleaning.*—Persistent, self-cleaning after several weeks.
- *Longevity.*—Individual flowers stay fresh on the plant for about 2 weeks. Inflorescences are ornamental for several weeks.
- *Fragrance.*—None detected.

Sterile flower:
- *Bud shape.*—Globose.
- *Bud length.*—2 mm.
- *Bud diameter.*—2 mm.
- *Bud color.*—RHS Green-White 157C.
- *Flower aspect.*—Outward.
- *Flower length.*—5 mm.
- *Flower Diameter.*—5 mm.
- *Flower shape.*—Cruciform.
- *Persistence.*—Persistent.

Sterile flower petals:
- *Petal arrangement.*—Cruciform.
- *Quantity.*—4.
- *Length of petal.*—2 mm.

*Width of petal.*—1 mm.
*Apex.*—Acute.
*Shape of petal.*—Narrow deltate.
*Petal margin.*—Entire.
*Petal base.*—Obtuse.
*Petal texture.*—Smooth, upper and under side.
*Color.*—Upper surface at first opening: RHS Green-White 157D. Under surface at first opening: RHS Green-White 157D. Upper surface at maturity: RHS Green-White 157D. Under surface at maturity: RHS Green-White 157D.

Sterile flower sepal:
*Arrangement.*—Cruciform.
*Number.*—4.
*Shape.*—Obovate.
*Tip.*—Obtuse.
*Base.*—Acute.
*Margin.*—Entire.
*Length.*—1 cm.
*Width.*—9 mm.
*Texture, upper.*—Smooth.
*Texture, lower.*—Smooth.
*Color.*—Upper surface at first opening: RHS Green-White 157D. Under surface at first opening: RHS Green-White 157D. Upper surface at maturity: RHS White 155A. Late Summer strongly flushed 61B. Maturing to have a flush near Greyed-Purple 186 and 186D. Under surface at maturity: RHS White 155A. Late Summer strongly flushed 59D. Maturing to have a flush near Red-Purple 63B. Upper surface, at most mature: RHS Greyed-Purple 186 and 186D. Under surface, at most mature: RHS Greyed-Purple 186 and 186D.

Sterile flower pedicel:
*Length.*—1.5 cm.
*Diameter.*—1 mm.
*Angle.*—90-130°.
*Strength.*—Flexible.
*Texture.*—Some pubescence.
*Color.*—RHS Greyed-Green 193C.

Fertile flower:
*Shape.*—Rotate.
*Depth.*—5 mm.
*Diameter.*—7 mm.
*Flower aspect.*—Outward.
*Persistence.*—Self-Cleaning.
*Longevity.*—1-2 weeks.
*Bud shape.*—Orbicular.
*Bud length.*—3 mm.
*Bud diameter.*—3 mm.
*Bud texture.*—Glabrous.
*Bud color.*—RHS Green-White 157C.

Fertile flower petals:
*Arrangement.*—Rotate to cruciform.
*Quantity.*—4.
*Length of petal.*—3 mm.
*Width of petal.*—2 mm.
*Apex.*—Acute.
*Shape of petal.*—Elliptic.
*Petal margin.*—Entire.
*Petal base.*—Truncate.
*Petal texture.*—Smooth, upper and under side.
*Color.*—Upper surface at first opening: RHS White 155C. Under surface at first opening: RHS White 155C. Upper surface at maturity: RHS White 155C. Under surface at maturity: RHS White 155C.

Fertile flower sepal:
*Arrangement.*—Cruciform.
*Quantity.*—4.
*Length.*—1 mm.
*Width.*—1 mm.
*Apex.*—Obtuse.
*Shape.*—Orbicular.
*Margin.*—Entire.
*Base.*—Truncate.
*Texture.*—Smooth, upper and under side.
*Color.*—Upper surface at first opening: RHS Yellow-Green 145C. Under surface at first opening: RHS Yellow-Green 145C. Upper surface at maturity: RHS Yellow-Green 145C. Under surface at maturity: RHS Yellow-Green 145C.

Fertile flower pedicel:
*Angle.*—90° to 130°.
*Strength.*—Moderate.
*Length.*—5 mm.
*Width.*—1 mm.
*Texture.*—Slight pubescence.
*Color.*—RHS White 155C.

REPRODUCTIVE ORGANS

Sterile flowers androecium: Present.
Stamens: 6 to 0 mm, Inconspicuous, about 1 mm.
Filament: Colored near White NN155A.
Anthers: Less than 1 mm long, colored near White NN155A.
Sterile flowers gynoecium: Not present.
Fertile flowers:
Stamens:
*Number.*—8.
*Filament length.*—3 mm.
*Filament color.*—RHS White 155C.

Anthers:
*Shape.*—Globular.
*Length.*—<1 mm.
*Color.*—RHS White 155C.
*Pollen color.*—RHS White 155c.
*Pollen amount.*—Moderate.

Pistil:
*Number.*—1.
*Length.*—Less than 1 mm.
*Style.*—Length: About 0.5 mm. Color: RHS Yellow-Green 145D.
*Stigma.*—Shape: Lobed. Color: RHS Yellow-Green 145D.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 3 to 9.

What is claimed is:

1. A new and distinct cultivar of *Hydrangea* plant named 'SMNHPH' as herein illustrated and described.

* * * * *